United States Patent [19]

Hercend et al.

[11] Patent Number: 4,772,552

[45] Date of Patent: Sep. 20, 1988

[54] MONOCLONAL ANTIBODY WHICH RECOGNIZES A 200-220 KD ANTIGEN ON NATURAL KILLER CELLS

[75] Inventors: Thierry Hercend, Paris, France; Jerome Ritz, Lincoln; Stuart F. Schlossman, Newton Centre, both of Mass.

[73] Assignee: Dana-Farber Cancer Institute, Inc., Boston, Mass.

[21] Appl. No.: 603,181

[22] Filed: Apr. 23, 1984

[51] Int. Cl.⁴ .................. C07K 15/04; C12N 5/00; G01N 33/577

[52] U.S. Cl. .......................................... 435/7; 435/4; 435/68; 435/172.2; 435/240.27; 935/95; 935/104; 935/107; 935/108; 436/506; 436/519; 436/548; 436/821; 530/387

[58] Field of Search ................. 530/387, 389; 435/68, 435/172.2, 240, 7, 29, 4, 948, 2; 935/95, 104, 107, 108, 110; 436/506, 519, 548, 804, 819, 821

[56] References Cited

U.S. PATENT DOCUMENTS

| | | | |
|---|---|---|---|
| 4,364,936 | 12/1982 | Kung | 424/85 |
| 4,572,834 | 2/1986 | Stout | 424/86 |
| 4,599,304 | 7/1986 | Lanier | 435/7 |
| 4,599,307 | 7/1986 | Saunders | 435/34 |
| 4,607,007 | 8/1986 | Lanier | 435/7 |

OTHER PUBLICATIONS

Rumpold, H. et al., Journal of Immunology 129(4):1458-1464 (Oct. 1982).
Vallera, D. A. et al., Journal Exper. Medicine 155:949-954 (3-1982).
Vallera, D. A. et al., Recent Advances in Bone Marrow Transplantation, Alan R. Liss Inc., N.Y. (1983), pp. 209-222.
Hercend, T. et al., J. Immunology 129:1299-1305 (9-1982).
Nieminen, P. et al., Journal of Immunology, 128(3):1097-1101 (Mar. 1982).
Fast, L. D. et al., Journal of Immunology, 127(2):448-452 (Aug. 1981).
Ako, T. et al., Journal of Immunology, 127(3):1024-1029 (Sep. 1981).
Zarling, J. M. et al., Journal of Immunology, 127(6):2575-2580 (Dec. 1981).
Hercend et al., (Jul., 1984) Chem. Abst., vol. 101:37050w.
Griffin et al., (1983) J. Immunol. 1,302,947.
Hercend et al., (1985) Chem. Abst., vol. 102:202224m.
Sun et al., Abstract, (15 Immuno-Chemistry 1983 98:32614A).
Zarling and Kung (1980) Nature 288, 394.
Griffin et al., (1983) J. of Immun. 130(6), pp. 2947-2951.
Perussia et al., (1983) J. of Immun. 130(5), pp. 2133-2141.
Herberman et al., (1981) Science 214, 24-30.
Itoh et al., (1983) Blood 61(5), 940-948.

Primary Examiner—Margaret Moskowitz

[57] ABSTRACT

Monoclonal antibody which lyses human natural killer (NK) cells in vitro in the presence of complement and which cells having a molecular weight of about 200-220 KD, as determined by SDS-PAGE electrophoresis on a 10% polyacrylamide gel.

14 Claims, No Drawings

MONOCLONAL ANTIBODY WHICH RECOGNIZES A 200–220 KD ANTIGEN ON NATURAL KILLER CELLS

BACKGROUND OF THE INVENTION

This invention relates to monoclonal antibodies.

Human peripheral blood contains a sub-population of mononuclear cells called natural killer (NK) cells, which are defined by their ability to lyse tumor cells in vitro in the absence of antibody or previous immunization.

Griffin et al. (1983) J. Immunol. 130, 2947, hereby incorporated by reference, describes a monoclonal antibody to NK cells (designated "N901") which is unreactive with non-NK human monocytes, granulocytes, B lymphocytes, T cells, erythrocytes, and platelets. The antibody is incapable of lysing NK cells and NK-like cells in vitro in the presence of complement. (As used herein, the term "NK-like cells" refers to cells found elsewhere than in normal peripheral blood, e.g., cultured NK cells, or cells in other organs or in malignancies, and either having the lytic capability of NK cells, or bearing a surface antigenic determinant specific to NK cells.)

Perussia et al. (1983) J. Immunol. 130, 2133, hereby incorporated by reference, describes another monoclonal antibody reactive with NK cells.

SUMMARY OF THE INVENTION

In general, the invention features, in one aspect, a monoclonal antibody capable of lysing human NK cells in vitro in the presence of complement.

In preferred embodiments, the antibody is unreactive with non-NK human granulocytes, non-NK human monocytes, human red blood cells, human platelets, human thymocytes, and non-NK human T3 lymphocytes; the antibody is of the IgM or IgG$_2$ isotype; and it recognizes an approximately 200,000–220,000 dalton NK cell-specific antigenic determinant on the surface of substantially all NK cells (that particular antigenic determinant is referred to herein as "NKH1$_4$".)

The antibody of the invention ("anti-NKH1$_4$") can be labeled, e.g. with a radioactive or fluorescent label, and used to identify NK cells and to distinguish these cells from non-NK cells. The antibody can also be used to destroy NK cells in tissue, e.g., bone marrow, to be infused in a patient, to inhibit graft-versus-host disease.

All monoclonal antibodies having the above specificity and characteristics are encompassed by the present invention. These monoclonal antibodies are produced by hybrid cells made using conventional hybridization and screening techniques such as are described in Reinherz et al. (1979) J. Immunol. 123, 1312 and Ritz et al. Nature (1980) 283, 583, hereby incorporated by reference. As is well-known in the monoclonal antibody field, each independently-produced hybrid cell line that produces a monoclonal antibody specific to the same particular antigenic determinant is nonetheless different from all others, as is each of the monoclonal antibodies so produced. Thus, while repetition of the procedure described below can result in the production of a hybrid cell line that produces a useful monoclonal antibody specific to and capable of lysing NK cells, it is highly unlikely that it will produce a cell line that produces a monoclonal antibody which is chemically an exact copy of the monoclonal antibody described below.

DESCRIPTION OF THE PREFERRED EMBODIMENTS

We now turn to a description of the preferred embodiments of the invention.

HYBRIDOMA PRODUCTION AND SCREENING

Six week old female Balb/c mice were immunized with cells of the human cloned NK cell line JT3, described in Hercend et al. (1983) Nature 301, 158. The JT3 clone was derived from purified large granular lymphocytes (LGL) initially stimulated with PHA and medium containing interleukin-2. For greater than 18 months, JT3 cells have been maintained in culture and have been found to display stable phenotype (T3-T4-T8-T11+N901+) and cytotoxic activity when tested against a large panel of in vitro established cell lines.

The JT3 clone was generated according to the limited dilution method described in Hercend et al. (1982) J. Immunol. 129, 1299 and Hercend et al. (1983) Nature 301, 158. The method involved cloning LGL at one cell/well on a feeder layer of autologous irradiated (5000 rad) human peripheral blood mononuclear cells (PBMC) plus either PHA (2 μg/ml) or allogeneic or autologous irradiated (5000 rad) EBV transformed B cells. Selected colonies were expanded by addition of culture medium containing LCM (10–15% final dilution) every 3 days. Culture medium was RPMI 1640 supplemented with 1% penicillin-streptomycin, 1% sodium pyruvate, 20% human AB serum. The JT3 line was subsequently subcloned 2 times at 100 cells/well on a feeder layer of autologous irradiated PBMC plus irradiated EBV transformed B cells. Following subcloning procedures, both phenotype and cytotoxic function have remained stable.

The immunization schedule consisted of an initial intraperitoneal injection of 4×10$^6$ JT3 cells emulsified in complete Freund's adjuvant (Difco, Detroit, Mich.) followed by two weekly intraperitoneal injections of 4×10$^6$ viable cells in phosphate buffered saline (PBS). Two weeks later, 2×10$^6$ cells were injected intravenously, followed by splenectomy 3 days later. Somatic cell hybridization was carried out by the method of Kohler and Milstein (1975) Nature 256, 495.

The initial screening of hybridoma supernatants was carried out as follows: 10,000 $^{51}$Cr labeled JT3 cells were incubated with an aliquot of each hybridoma supernatant for 30 minutes at room temperature in V bottom microtiter plates. Rabbit complement at an appropriate non-toxic dilution (usually 1:10) was then added for 1 hour at 37° C. Subsequently, plates were spun down and antibody reactivity was measured as release of $^{51}$Cr into the supernatants using a gamma scintillation counter. Positive supernatants were then tested under identical experimental conditions against an autologous MHC restricted cytotoxic T cell clone as well as an autologous EBV transformed B cell line. Cells were selected which produced antibodies which, in the presence of complement, lysed JT3 cells but not the MHC restricted cytotoxic T cell clone or the EBV transformed B cell line. Antibody producing hybridomas were subsequently recloned two times by limiting dilution and immune ascites were produced.

ANTIBODY CHARACTERIZATION

The reactivity pattern of the antibody was determined by testing on purified populations of lymphoid and nonlymphoid cells by indirect immunofluorescence assays and subseqeunt analysis using either a FACS I or Epics V flow cytometer. To obtain suitable cells for testing, PBMC were isolated from healthy volunteer donors by Ficoll-Hypaque (F/H) density gradient centrifugation. Monocyte enriched adherent cells were obtained from PBMC by two step adherence on plastic culture dishes. Granulocytes were isolated from F/H gradient pellets using high molecular weight dextran. Activated T cells were generated by stimulating E+ cells with phytohemagglutinin (PHA) (2 µg/ml) and tested on day 7 following stimulation.

The antibody was found to be strongly reactive with JT3 immunizing cells. In addition, as shown in the Table below, it was found to react with a small (12%) population of lymphocytes present in peripheral blood. Human monocytes, granulocytes, platelets, red blood cells, thymocytes, T3 lymphocytes, and PHA activated E+ cells were negative.

TABLE

| Peripheral blood lymphocytes | | | | |
|---|---|---|---|---|
| Donor | % reactive cells with anti-NKH1$_A$ | Donor | % reactive cells with NKH1$_A$ | Mean ± SD |
| 1 | 9 | 7 | 10 | 12.3 ± 4 |
| 2 | 17 | 8 | 20 | |
| 3 | 8 | 9 | 17 | |
| 4 | 13 | 10 | 15 | |
| 5 | 12 | 11 | 9 | |
| 6 | 15 | 12 | 11 | |

A further experiment demonstrated that anti-NKH1$_A$ was unreactive with all the cells in a series of fourteen lymphohematopoietic cell lines derived either from virally transformed cells or tumor cells.

Morphology of NKH1$_{A+}$ cells in unstimulated peripheral blood was determined following purification of these cells by immunofluorescence cell sorting. For this purpose, peripheral blood lymphocytes from two individual donors were incubated with anti-NKH1$_A$ plus GM-FITC. Small numbers (about 50,000) of NKH1$_{A+}$ cells were then purified using an Epics V cell sorter and cytocentrifuge smears were prepared and analyzed. It was found that NKH1$_{A+}$ purified fractions consisted almost entirely (over 90%) of large granular lymphocytes. This finding was consistent with previous studies that have demonstrated that virtually the entire NK activity present in peripheral blood was mediated by a small fraction of lympocytes which can be identified morphologically because of their larger size and the presence of azurophilic granules in the cytoplasm.

CELL LYSIS

Since anti-NKH1$_A$ is an IgM antibody, it was possible to investigate its capacity for lysing NK cells in human peripheral blood in the presence of complement. For this purpose, peripheral blood mononuclear cells were incubated with either medium or anti-NKH1$_A$ for 30 minutes at room temperature. Anti-N901 (discussed above), which is a nonlytic IgG$_1$ antibody directed at NK cells, was used as a control in these experiments. Antibody excess was washed out and complement was then added for 45 minutes at 37° C. This procedure was repeated two times. Subsequently, remaining viable cells were counted and $^{51}$Cr labeled target cells were added.

This procedure was used on PBL target cells from a donor displaying a very high level of spontaneous cytotoxicity against a T cell leukemia line, indicating the presence of many NK cells. Treatment of these PBL with anti-NKH1$_A$ plus complement was followed by a virtually complete loss of NK activity, indicating that anti-NKH1$_A$ reacted with all NK cells in peripheral blood. Control-treated PBL displayed a continued high level of cytotoxicity.

CHARACTERIZATION OF NKH1$_A$ ANTIGEN

Immunoprecipitation experiments were conducted to identify the molecular weight of the antigen defined by anti-NKH1$_A$.

The immunoprecipitations were done using preformed complexes of rabbit anti-mouse Ig with anti-NKH1$_A$. These preformed complexes were reacted with $^{125}$I surface labeled JT3 cell lysates which were precleared 3 times by incubation at 4° C. for 1 hour with either formalin fixed Staph A bacteria and/or preformed complexes of rabbit anti-mouse Ig nonspecific monoclonal antibody. Aliquots of precleared lysate were then incubated with specific preformed complexes for 2 hours at 4° C. Immune precipitates were then washed 4 times with RIPA buffer and dissolved in sodium dodecyl sulfate polyacrylamide gel eletrophoresis (SDS-PAGE) sample buffer and loaded onto separate slots on a 10% polyacrylamide slab gel. Identical aliquots of immune precipitation were run in nonreduced and reduced conditions after addition of 2 mercaptoethanol to SDS-PAGE sample buffer. Gels were dried and radiolabeled precipitates were visualized using standard methods. Anti-NKH1$_A$ precipitated a broad band at approximately 200-220 KD. Additional experiments were performed in which the precipitates were analyzed using a 5-15% polyacrylamide gradient and no additional specific bands were identified. When gradient gels were used, the specific band was seen at a slightly lower molecular weight (180-200 KD) as compared to the 10% polyacrylamide gels.

It was demonstrated that anti-NKH1$_A$ and anti-N901 are probably directed at the same NK surface antigen molecule, in a series of competitive binding experiments. Advantage was taken of the different isotypes of the two antibodies (anti-NKH1$_A$ being an IgM and anti-N901 being an IgG$_1$). Using isotype specific FITC in indirect immunofluorescence assays, it was found that anti-N901 effectively blocked binding of anti-NKH1$_A$ whereas anti-NKH1$_A$ did not significantly affect binding of anti-N901. These results confirmed that both antibodies were specific for the same cell surface antigen and also suggested that the IgG$_1$ antibody (anti-N901) had a higher affinity than the IgM (anti-NKH1$_A$).

DEPOSIT

Cells producing anti-NKH1 have been deposited in the American Type Culture Collection, Rockville, Md., and are given ATCC Accession No. HB8564.

USE

Identification of NK cells and NK-like cells

The monoclonal antibody of the invention can be used to identify NK and NK-like cells in peripheral blood samples and in samples from other tissue, e.g. bone marrow.

The antibody can be used to detect such cells in clinical samples using any conventional immunoassay technique, e.g., indirect immunofluorescence or a direct assay employing antibody labeled, e.g., with a radioactive label.

The antibody can also be used to detect NK or NK-like cells, or cell-free antigen, in plasma and other body fluids in vitro.

Detecting and quantifying circulating NK cells can permit correlations between various disease states and numbers of NK cells; such information can in turn further elucidate the role of NK cells in healthy and sick individuals, a role which, evidence now suggests, may include the destruction of malignant cells.

THERAPY

Since NK cells may play a deleterious role in graft-versus-host disease (GVHD) following organ or tissue transplants, the antibody of the invention can be useful in combatting GVHD by killing associated NK cells. For example, in connection with a bone marrow transplant, the antibody plus complement can be used to treat the bone marrow prior to transplantation, according to conventional tecniques, to kill the NK cells which could otherwise contribute to rejection of the host by the bone marrow. The ability of the antibody to lyse NK cells in the presence of complement is a function of its being of the IgM isotype; generally, only IgM and IgG$_2$ antibodies possess this property. The kill rate of NK cells in tissue can be increased by employing antibody to which has been coupled, using conventional techniques, a cytotoxic agent such as ricin or adiamycin.

The selective in vivo removal of NK cells may also prove useful in the treatment of autoimmune diseases such as SLE which are in part mediated by NK cells.

The antibody may also prove useful in inhibiting the rejection of allografts such as bone marrow and kidneys by using anti-NKH1$_A$ to inactivate host NK cells which would otherwise attack the allograft.

Another use of the antibody is in the purification of NK cells from peripheral blood or from a cell suspension of hematopoietic tissue, e.g. bone marrow, or lymphoid tissue, e.g. thymus, spleen, or lymph node tissue. The antibody can be used for such purification in connection with any conventional cell separation technique, e.g. cell sorting, immune rosetting, panning, or immune affinity column chromotography.

Such purification of NK cells can be useful where a particular medical disorder requires the infusion into the patient of NK cells, either from the patient or from a donor. Such infusion of NK cells can be used, e.g., to treat malignancies susceptible to attack by NK cells.

It may prove particularly useful to use a patient's own NK cells for such treatment. After anti-NK is used to purify NK cells from the patient's blood or other tissue, a selected NK cell can be cultured and expanded and then reinfused into the patient; appropriate culture methods are described in Hercend et al. (1982) J. Immunol. 129, 1299; and Hercend et al. (1983) Nature 301, 158, both hereby incorporated by reference.

Other embodiments are within the following claims. For example, the antibody can be labeled in a variety of ways, e.g. with fluorescein-containing ligands, heavy metals, or $^{13}$C-containing compounds.

We claim:

1. A monoclonal antibody which lyses human natural killer cells in vitro in the presence of complement, said antibody recognizing an antigenic determinant on the surface of human natural killer cells having a molecular weight of about 200-220 KD as determined by SDS-PAGE electrophoresis on a 10% polyacrylamide slab gel.

2. The antibody of claim 1, said antibody being unreactive with non-natural killer human granulocytes, non-NK human monocytes, human red blood cells, human thymocytes, and non-natural killer human T3 lymphcytes.

3. The antibody of claim 1, said antibody being of the IgM or IgG2 isotype.

4. The antibody of claim 1, coupled to a cytotoxic agent.

5. The antibody of claim 1, labeled with a detectable label.

6. The antibody of claim 5, said antibody being radiolabeled.

7. The antibody of claim 5, said antibody being fluorescently labeled.

8. The monoclonal antibody produced by the hybridoma cell ATCC HB8564.

9. A hybridoma cell which produces the monoclonal antibody of claim 4.

10. The hybridoma cell line ATCC HB8564.

11. A method of detecting the presence of natural killer or natural-killer-like cells in a human patient comprising contacting a cell-containing clinical sample from said patient with the antibody of claim 1 for a time and under conditions sufficient to form immune complexes between said antibody and said natural killer or natural-killer-like cells in said sample, and detecting immune complexes as an indication of the presence of said cells.

12. A method of lysing natural killer or natural-killer-like cells in a clinical sample comprising incubating said sample with the antibody of claim 1 in the presence of complement for a time and under conditions sufficient to cause lysis of said cells in said sample.

13. A method of lysing natural killer cells or natural-killer-like cells in a clinical sample comprising contacting said sample with the cytotoxic agent-coupled antibody of claim 4 for a time and under conditions sufficient to cause lysis of said cells in said sample.

14. The method of claim 12 or claim 13 wherein said clinical sample is a bone marrow sample, and, following said lysing, said sample is reinfused into a patient.

* * * * *

UNITED STATES PATENT AND TRADEMARK OFFICE
CERTIFICATE OF CORRECTION

PATENT NO. : 4,772,552

DATED : September 20, 1988

INVENTOR(S) : Thierry Hercend et al.

It is certified that error appears in the above-identified patent and that said Letters Patent is hereby corrected as shown below:

On the face of the patent, in the Abstract, line 3, after "which", insert --recognizes an antigenic determinant on the surface of human NK--;

Col. 5, line 20, "techniques" is misspelled;

Col. 6, claim 2, line 3, delete "NK" and insert --natural killer--.

Signed and Sealed this

Thirty-first Day of January, 1989

Attest:

DONALD J. QUIGG

*Attesting Officer*  *Commissioner of Patents and Trademarks*

UNITED STATES PATENT AND TRADEMARK OFFICE
CERTIFICATE OF CORRECTION

PATENT NO. : 4,772,552

DATED : September 20, 1988

INVENTOR(S) : Thierry Hercend, Jerome Ritz and Stuart F. Schlossman

It is certified that error appears in the above-identified patent and that said Letters Patent is hereby corrected as shown below:

Insert at Column 4, line 1 the following:

"This invention was made with U.S. government support under grants no. CA28740, CA25369-05, AI12069-10, and CA34183-01 awarded by the National Institutes of Health. The government has certain rights in the invention."

Signed and Sealed this

Fifteenth Day of March, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO.  : 4,772,552
DATED       : September 20, 1988
INVENTOR(S) : Thierry Hercend, Jerome Ritz and Stuart F. Schlossman It is certified that error appears in the above-indentified patent and that said Letters Patent is hereby corrected as shown below:

Insert at column 1, line 1, the following:

"This invention was made with U.S. government support
under grants no. CA28740, CA25369-05, AI12069-10, and
CA34183-01 awarded by the National Institutes of Health.
The government has certain rights in the invention."

This Certificate supersedes Certificate of Correction issued March 15, 1994.

Signed and Sealed this

Nineteenth Day of July, 1994

Attest:

BRUCE LEHMAN

*Attesting Officer*     Commissioner of Patents and Trademarks